(12) United States Patent
Berry et al.

(10) Patent No.: US 6,248,128 B1
(45) Date of Patent: *Jun. 19, 2001

(54) EXPANDABLE INTRALUMINAL STENTS

(75) Inventors: Joel L. Berry; Carlos M. Ferrario; Richard H. Dean; Virginia S. Newman, all of Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/979,433

(22) Filed: Nov. 26, 1997

Related U.S. Application Data

(63) Continuation of application No. 08/309,359, filed on Sep. 21, 1994, now Pat. No. 5,702,419.

(51) Int. Cl.⁷ ..................................................... A61F 2/06
(52) U.S. Cl. ........................................ 623/1.17; 623/1.13
(58) Field of Search ................................ 606/108, 191.2; 623/1, 11, 12, 1.1, 1.13, 1.15–1.22

(56) References Cited

U.S. PATENT DOCUMENTS

| | | |
|---|---|---|
| 2,701,559 | 2/1955 | Cooper . |
| 3,657,744 | 4/1972 | Ersek . |
| 3,774,596 | 11/1973 | Cook . |

(List continued on next page.)

FOREIGN PATENT DOCUMENTS

| | | |
|---|---|---|
| 0183372 | 4/1986 | (EP) . |
| 0221570 | 1/1991 | (EP) . |
| 0483372 | 5/1992 | (EP) . |
| 9401164 | 4/1995 | (FR) . |
| 1205743 | 9/1970 | (GB) . |
| 8803752 | 11/1983 | (WO) . |

OTHER PUBLICATIONS

Cope, Constantin, "Stiff Fine–Needle Guide Wire for Catheterization and Drainage," Radiology 147:264, Apr. 1983.
W.R. Castaneda–Zuniga and S.M. Tadavarthy, Interventional Radiology, "New Stent Developments", pp. 553–597. Radiology 153P (Special Issue), p. 329 (mailed to public in Oct. 1984).
Lary et al., "The Experimental Use of Steel Mesh Tubes for the Replacement of Arterial Segments," AMA Archives of Surgery 72, pp. 69–75; 1956.
Johnson & Johnson, Nine Months' Report 1991, "Clogged Iliac Arteries Can Be Kept Open With A New Balloon–Expandable Stent."

(List continued on next page.)

*Primary Examiner*—Glenn K. Dawson
(74) *Attorney, Agent, or Firm*—Dann, Dorfman, Herrell and Skillman, P.C.

(57) ABSTRACT

An expandable, intraluminal stent is provided which can be inserted into a body passage, and is capable of supporting an intact vascular graft. The stent is a thin-walled, generally tubular member having a plurality of rigid support tabs spaced uniformly around the perimeter of the two ends of the stent. A plurality of spacer bars span longitudinally between the rigid support tabs at one end of the stent and corresponding rigid support tabs at the other end. The spacer bars serve as struts to prevent longitudinal expansion or contraction of the stent so that the length of the stent is maintained. Plastically deformable connecting links interconnect adjacent rigid support tabs around each end of the stent to enable the stent to be expanded to an enlarged diameter. The stent can be expanded with a delivery system which applies a radially, outwardly extending force from the exterior of the stent. Alternatively, the stent can be expanded using an angioplasty balloon.

47 Claims, 12 Drawing Sheets

U.S. PATENT DOCUMENTS

| | | |
|---|---|---|
| 3,868,956 | 3/1975 | Alfidi et al. . |
| 3,882,845 | 5/1975 | Bucalo . |
| 3,889,685 | 6/1975 | Miller, Jr. et al. . |
| 4,018,230 | 4/1977 | Ochiai et al. . |
| 4,140,126 | 2/1979 | Choudhury . |
| 4,183,102 | 1/1980 | Guiset . |
| 4,299,226 | 11/1981 | Banka . |
| 4,318,410 | 3/1982 | Chin . |
| 4,328,811 | 5/1982 | Fogarty . |
| 4,338,942 | 7/1982 | Fogarty . |
| 4,403,612 | 9/1983 | Fogarty . |
| 4,416,028 | 11/1983 | Eriksson et al. . |
| 4,425,908 | 1/1984 | Simon . |
| 4,483,339 | 11/1984 | Gillis . |
| 4,483,340 | 11/1984 | Fogarty et al. . |
| 4,503,569 | 3/1985 | Dotter . |
| 4,512,338 | 4/1985 | Balko et al. . |
| 4,553,545 | 11/1985 | Maass . |
| 4,560,374 | 12/1985 | Hammerslag . |
| 4,562,596 | 1/1986 | Kornberg . |
| 4,564,014 | 1/1986 | Fogarty et al. . |
| 4,580,568 | 4/1986 | Gianturco . |
| 4,592,341 | 6/1986 | Omagari et al. . |
| 4,619,261 | 10/1986 | Guerriero . |
| 4,650,466 | 3/1987 | Luther . |
| 4,733,665 * | 3/1988 | Palmaz ................................ 623/1.13 |
| 4,739,762 | 4/1988 | Palmaz . |
| 4,762,128 | 8/1988 | Rosenbluth . |
| 4,768,507 | 9/1988 | Fischell et al. . |
| 4,776,337 | 10/1988 | Palmaz . |
| 4,793,348 | 12/1988 | Palmaz . |
| 4,800,882 | 1/1989 | Gianturco . |
| 4,807,626 | 2/1989 | McGirr . |
| 4,893,623 | 1/1990 | Rosenbluth . |
| 4,902,508 | 2/1990 | Badylak et al. . |
| 4,907,336 | 3/1990 | Gianturco . |
| 5,035,706 | 7/1991 | Gianturco et al. . |
| 5,102,417 | 4/1992 | Palmaz . |
| 5,108,417 | 4/1992 | Sawyer . |
| 5,192,307 | 3/1993 | Wall . |
| 5,292,331 | 3/1994 | Boneau ................................ 606/198 |
| 5,360,443 * | 11/1994 | Barone et al. ....................... 623/1.13 |
| 5,403,341 | 4/1995 | Solar . |
| 5,411,507 | 5/1995 | Heckele . |
| 5,496,365 | 3/1996 | Sgro . |
| 5,522,881 * | 6/1996 | Lentz ................................ 623/1.13 |
| 5,549,663 * | 8/1996 | Cottone ................................ 623/1.13 |
| 5,556,414 * | 9/1996 | Turi ........................................... 623/1 |
| 5,591,197 * | 1/1997 | Orth et al. ........................... 606/198 |
| 5,609,626 * | 3/1997 | Quijano et al. ...................... 623/1.13 |
| 5,630,829 | 5/1997 | Lauterjung . |
| 5,693,085 * | 12/1997 | Buirge et al. ........................... 623/1 |
| 5,702,419 * | 12/1997 | Berry et al. ........................... 606/198 |
| 5,733,303 * | 3/1998 | Israel et al. ........................... 606/198 |
| 5,755,781 | 5/1998 | Jayaraman . |

OTHER PUBLICATIONS

Dotter, "Transluminally–placed Coulspring Endarterial Tube Grafts", Investigative Radiology, Sep.–Oct. 1969, 4, pp. 329–332.

Maass et al., "Radiological Follow–up of Transluminally Inserted Vascular Endoprostheses:An Experimental Study Using Expanding Spirals",Radiology 152,pp.659–663, 198.

Duprat et al., "Flexible Balloon–expended Stent for Small Vessels—Work in Progress", Radiology 162(1), pp. 276–278; 1987.

Palmaz et al., "Atherosclerotc Rabbit Aortas: Expandable IntraluminalGrafting", Radiology 160, pp. 723–726, 1986.

D. Liermann et al., "The strecker Stent: Indications and Results in Iliac and Femoropopliteal Arteries". Cardopvasc Intervent Radiol (1992) 15:298–305.

J.C. Palmaz, "Intravascular Stenting: From Basic research to Clinical Application", Cardiovasc Intervent Radiol (1992) 15:279–284.

J.C. Palmaz, "Intravascular Stents: Tissue–Stent Interactions and design Considerations", AJR (1993) 160:613–618.

C. Zollikofer et al., "Historical Overview on the Development and Characteristics of Stents and Future Outlooks", Cardiovasc Intervent Radiol (1992) 15:272–278.

J.C. Palmaz et al., "Expandable Intraluminal Graft: A Preliminary Study", Radiology 156, pp. 73–77, 1985.

Wright et al., "Percutaneous Endovascular Stents: An Experimental Evaluation", Radiology 156, pp. 69–72, 1985.

Dotter et al., "Transluminal Expandable Nitinol Coil Stent Grafting: Preliminary Report", Radiology 147, p. 259.

Cragg et al., "Non surgical Placement of Arterial Endoprostheses: A New Technique Using Nitinol Wire", Radiology 147; 1983, pp. 261–263.

* cited by examiner

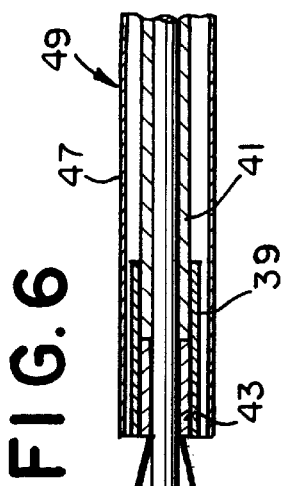
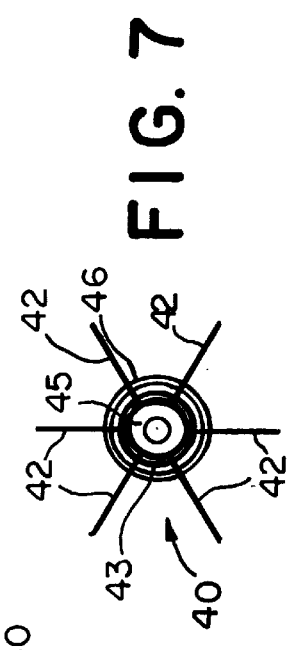
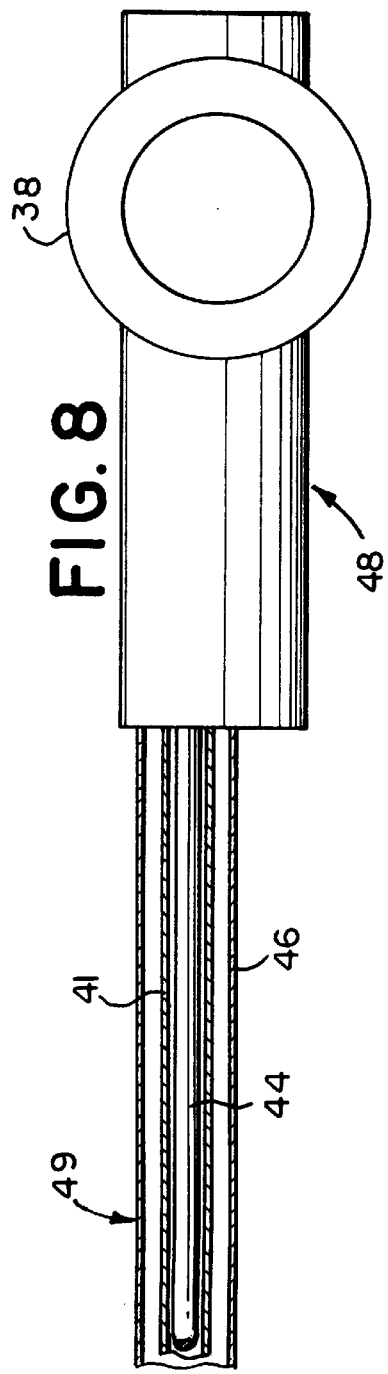

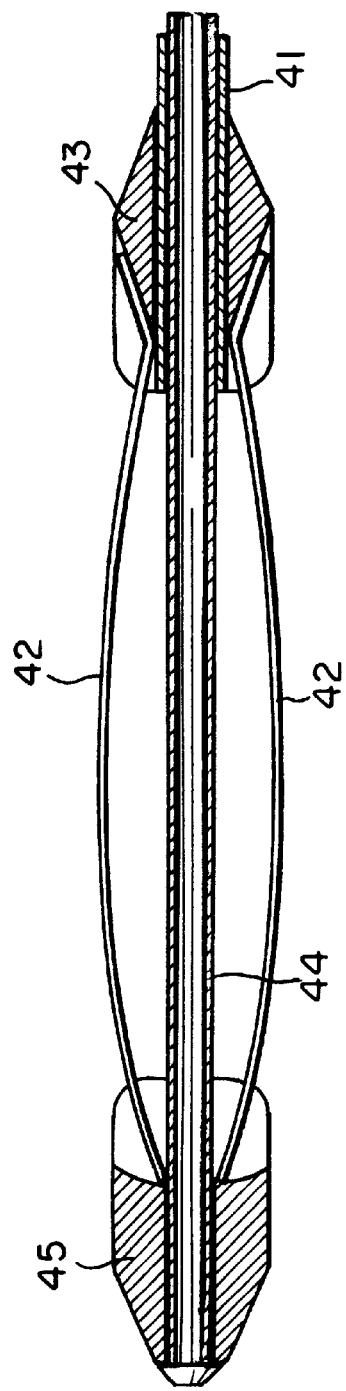
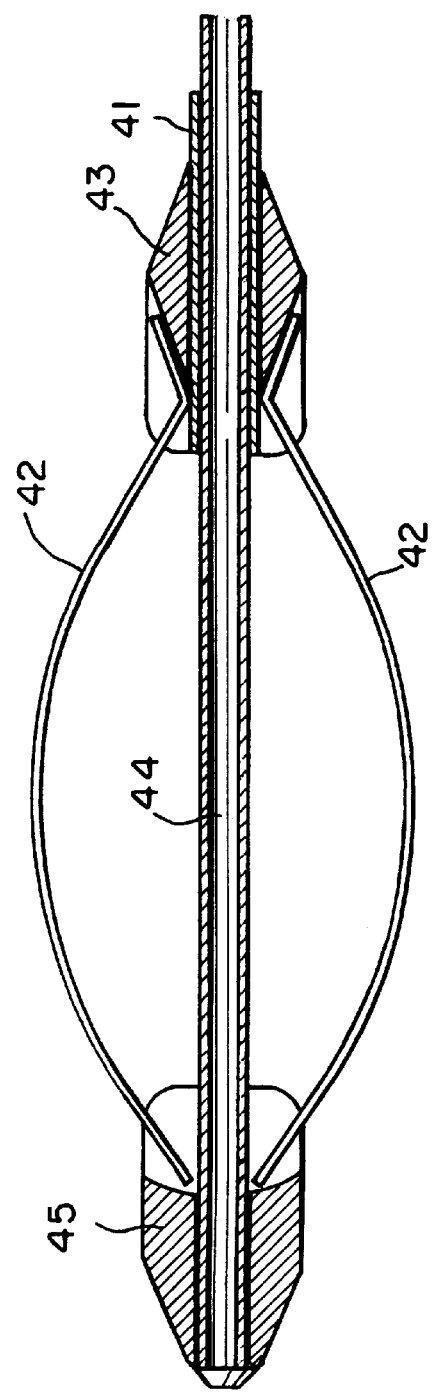

EXPANDABLE INTRALUMINAL STENTS

This is a continuation of application Ser. No. 08/309,359, filed Sep. 21, 1994, now U.S. Pat. No. 5,702,419 which is hereby incorporated by reference.

FIELD OF THE INVENTION

The present invention relates to an expandable, intraluminal stent and an apparatus and a method for deploying the expandable, intraluminal stent in a body passage. More particularly, the present invention relates to a type of intraluminal stent capable of supporting an intact, intraluminal, venous graft providing an inner stent lining having an endothelial layer and an apparatus and method for deploying and mechanically expanding the vein-lined stent within a body passage through the application of an outward force on the external surface of the stent.

BACKGROUND OF THE INVENTION

As an alternative to vascular surgery, balloon angioplasty has been a common method for unblocking narrowed or occluded blood vessels. In this procedure, an angioplasty balloon is inflated within a stenosed vessel in order to dilate the vessel to provide an enlarged lumen. Although balloon angioplasty has been successful in restoring flow in stenotic or occluded vessels, these vessels often restenose due to elastic recoil of the diseased tissue. Subintimal dissection is also caused by balloon induced stresses and results in geometric irregularities at the inner wall leading to flow disturbances and decreased flow.

Consequently, intraluminal stenting has been used with increasing frequency to improve the success rate of transluminal balloon angioplasty. These tubular stents are introduced via catheter, expanded to a preset diameter and left in situ to resist elastic recoil and to hold dissections against the vessel wall. There are essentially three types of conventional stents all of which are metallic. The three types are balloon expandable, self-expandable, and memory metals (i.e., nitinol). The balloon-expandable stents deform plastically beyond the elastic limit of the material and are relatively rigid at their expanded diameter. The balloon expandable stents are mounted over a deflated angioplasty balloon and then positioned within a vessel. The balloon is then inflated transmitting outward radial forces across the tubular stent that plastically deforms into a final larger diameter against the vessel wall. The balloon is then deflated and removed from the vessel. Self-expandable stents rely on the potential energy stored in a reduced diameter to spring back to some new, larger diameter when released. Self-expandable stents tend to be more compliant than balloon-expandable stents. Self-expandable stents are compressed into a smaller diameter and then inserted into a sheath. The sheath is then inserted into a vessel and removed at the desired location to expose the stent. The compressed stent springs open against the vessel wall exerting a constant outward force thereby fixing the stent in place. Memory metal or nitinol stents assume a final enlarged diameter from an initial reduced diameter in the presence of temperature changes. Nitinol stents, along with resorbable polymeric stents, are not as widely used as balloon- and self-expandable stents. Memory metal stents respond to temperature changes by changing from a reduced diameter to a final expanded configuration at the stenotic site.

Although patency rates have improved when stenting is used in conjunction with balloon angioplasty, thrombosis and neointimal hyperplasia within the region of the stent continue to compromise the potential utility of these devices. Stent surface thrombogenicity and processes regulating neointimal hyperplasia are considered to be major contributors to the long-term problems associated with conventional stenting.

Ultimately, endothelialization of the stent surface properly represents the best chance for successful use of a stent since the endothelial layer has the potential to inhibit low-flow thrombosis and to moderate factors involved in maintaining luminal patency. The course of events leading to endothelialization of any metallic stent surface begins with thrombus formation at the stent surface. The thrombogenicity of the stent surface is dependent on surface characteristics such as the electronegative potential of the metal and surface roughness. Thrombus that initially forms is eventually replaced by fibromuscular tissue, fibrocytes and collagen. Endothelialization is allowed to proceed across the newly formed tissue from the endothelial cells exposed between the stent latticework and from the ends of the stent. The extent to which endothelialization occurs depends upon the number of cells to survive the trauma of stent deployment as well as the flow conditions set up by the introduction of the stent. Minimization of mechanically induced trauma to the endothelial lining of the vessel certainly becomes desirable. Accordingly, a stent design achieving a low ratio of metal surface area to open surface area therefore becomes desirable to reduce thrombogenicity while maximizing the potential for endothelialization.

Another factor to be considered is that blood flow is altered by the presence of a stent. Troughs created along the stented segment of the vessel create turbulence, boundary layer separation, and regions of potentially low flow and low shear. These kinds of flow conditions have been implicated as a mechanism for atherogenesis. Accordingly, a stent having an open structural design appears to be desirable.

Next, most conventional stents undergo longitudinal shortening with an increase in diameter. In the presence of arterial smooth muscle contraction/relaxation and pulsatile flow, length changes likely accompany diameter changes. Endothelium may be sloughed as a result and an additional inflammatory reaction may ensue due to relative motion at the stent-tissue interface. The foreshortening of conventional stents within the target location also creates problems in deployment accuracy and potentiates further damage to the wall of the vein at the target location. Accordingly, reducing or eliminating longitudinal shortening of the stent during expansion also becomes a desirable goal.

It is well known that the endothelial layer, formed by the cells lining the inner wall of a vessel, is a dynamic layer that is able to produce, secrete, and modulate factors involved in maintaining patency of the vessel lumen. These endothelial properties are thought to be the reason venous conduits have significantly higher patency rates than synthetic grafts when used in arterial reconstructions. combining the properties of endothelium and stents would therefore be desirable to create a better endoprosthesis. Specifically, a stent lined with an endothelial layer would be less thrombogenic. Additionally, the vessel wall, which is likely to be injured by the angioplasty, would be largely shielded from blood-borne components such as platelets which are known to be potent instigators of neointimal hyperplasia. Lastly, the stent itself would still retain its ability to counteract the elastic recoil of the vessel wall following angioplasty.

Accordingly, it would be highly desirable to have a stent that reduces surface contact with the vessel wall, that inhibits longitudinal shortening during expansion and that supports a venous lining to provide an inner endothelial layer.

SUMMARY OF THE INVENTION

In accordance with the present invention, an expandable, intraluminal stent is provided for deployment in a body passage, such as a blood vessel, to inhibit vessel stenosis. The stent in accordance with the present invention is easy to deploy, is made of metal so that it can be imaged during deployment, demonstrates a high expansion ratio, counteracts elastic recoil of the vascular wall, and has a non-thrombogenic surface. Furthermore, because of its unique configuration, the stent does not shorten following expansion. The stent also enables vein grafts or other biocompatible materials or surfaces to be mounted within its lumen without compromise of endothelial integrity or creation of vein graft redundancy.

A stent delivery system and method are also provided in accordance with the present invention for introducing and deploying the stent within a selected body passage such as a constricted, diseased or injured vascular site. Generally, the stent is deployed by a mechanism that exerts an outward force on the external surface of the stent to expand the stent to an enlarged diameter, thereby leaving its luminal environment undisturbed.

The stent is a generally thin-walled, meshlike, tubular structure having a central lumen. The stent includes a plurality of rigid support tabs, in the form of end supports, which are positioned in an annular arrangement to form a ring at each end of the stent. The rigid support tabs are uniformly spaced around the periphery of each end of the stent. As a result, the rigid end supports are disposed in the respective ring so that each end support is positioned diametrically opposed to another one of the end supports in the ring. The rigid support tabs at one end of the stent are disposed generally opposite corresponding rigid support tabs at the other end of the stent. A plurality of spacer bars, in the form of rigid struts, are used to connect the rigid support tabs at the one end of the stent to the opposite rigid support tabs at the other end of the stent. The spacer bars span longitudinally between the support tabs and serve as struts to maintain the length of the stent. A plurality of plastically deformable connecting links are used to interconnect adjacent support tabs along the circumference of each end of he stent, so that the stent is expandable to an enlarged diameter through plastic deformation of the connecting links which thereby serve to maintain the stent in its expanded configuration. When in the enlarged diameter, the surface area of the stent is at least 70%, and alternatively at least 80%, open.

A further feature of the present invention is that an endothelial layer provided by a vein segment can be attached to the stent prior to deployment of the stent. The vein segment can be positioned within the central lumen of the stent and then attached to the stent using sutures.

The stent delivery apparatus comprises a drive unit and a catheter having a stent deployment mechanism. The stent deployment mechanism is disposed at the distal end of the stent delivery apparatus and is designed to expand the stent by applying a radially, outwardly extending force from the exterior of the stent. The stent deployment mechanism is operably connected to the drive unit so that operation of the drive unit controls operation of the stent deployment mechanism.

The stent deployment mechanism comprises a uniform bundle of spokes attached to the distal end of a control cable that interconnects the deployment mechanism with the drive unit. Free ends of the spokes are passed through corresponding coupling tubes attached to the exterior of the stent for releasably coupling the spokes to the stent. The free ends of the spokes are then loosely held in place by a conical tip which is attached to the distal end of a central guidewire from the control cable. The guidewire is coaxial with an outer flexible tube and is freely movable within the flexible tube. The guidewire extends from the flexible tube and passes through the lumen of the stent along a central axis of the bundle of spokes. Movement of the guidewire into the flexible tube causes the spokes to flex outwardly thereby exerting an outward external force on the stent causing the stent to dilate. Subsequent movement of the guidewire out of the tube causes the free ends of the spokes to spring free of the conical tip. Withdrawal of the stent deployment mechanism away from the expanded stent then causes the freed spokes to disengage from the coupling tubes of the stent.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 6 is an enlarged side elevational view of the stent deployment mechanism, with several wire spokes removed, located at the distal end of the delivery apparatus used to deploy the stent in the body passage;

FIG. 7 is an enlarged end elevational view of the stent deployment mechanism located at the distal end of the delivery apparatus used to deploy the stent in the body passage;

FIG. 8 is an enlarged plan view of the drive unit located at the proximal end of the delivery apparatus used to deploy the stent in the body passage;

FIG. 9a is an enlarged, schematic cross sectional view of the stent deployment mechanism at the distal end of the delivery apparatus with a pair of the wire spokes shown in an unflexed position;

FIG. 9b is an enlarged, schematic cross sectional view of the distal end of the delivery apparatus with a pair of the wire spokes shown in a flexed position;

DETAILED DESCRIPTION OF THE PREFERRED EMBODIMENTS

Figure 1:
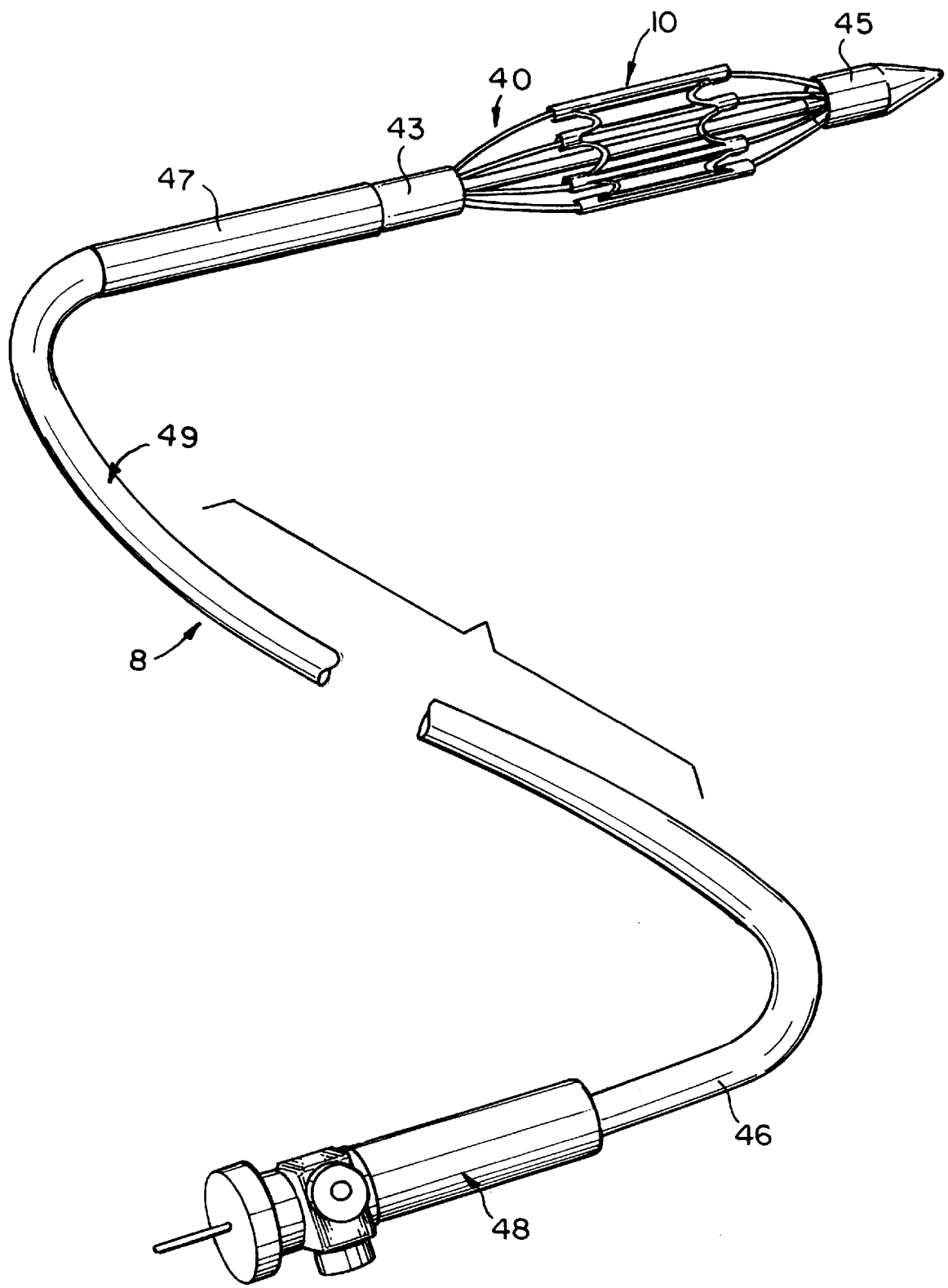
FIG. 1 is an enlarged perspective view of an expandable intraluminal stent in accordance with the present invention and a delivery apparatus also in accordance with the present invention for inserting the stent into the lumen of a body passage and for expanding the stent.

Referring to FIG. 1, a stent delivery apparatus, generally designated 8, is depicted for deploying a generally tubular, thin-walled stent 10 within a selected body passage such as a stenosed vessel. The stent delivery apparatus 8 serves as a catheter for inserting the stent 10 into the selected body passage. For this purpose, the tubular stent 10 is removably mounted on a stent deployment mechanism, generally designated 40, in the form of a wire bundle disposed at a distal end of the stent delivery apparatus 8.

Control of the stent deployment mechanism 40 is effected by a manually-operable drive unit 48 in the form of a rack and pinion microdrive. The drive unit 48 is disposed at a proximate end of the stent delivery apparatus 8 and is attached to the stent deployment mechanism 40 by a flexible control cable 49. Manual operation of the drive unit 48 controls operation of the stent deployment mechanism 40 so that the stent 10 can be safely deployed at a selected target location within a body passage whereupon the stent deployment mechanism 40 and the control cable 41 are then withdrawn from the body leaving the stent 10 properly deployed at the target location.

Figure 2:
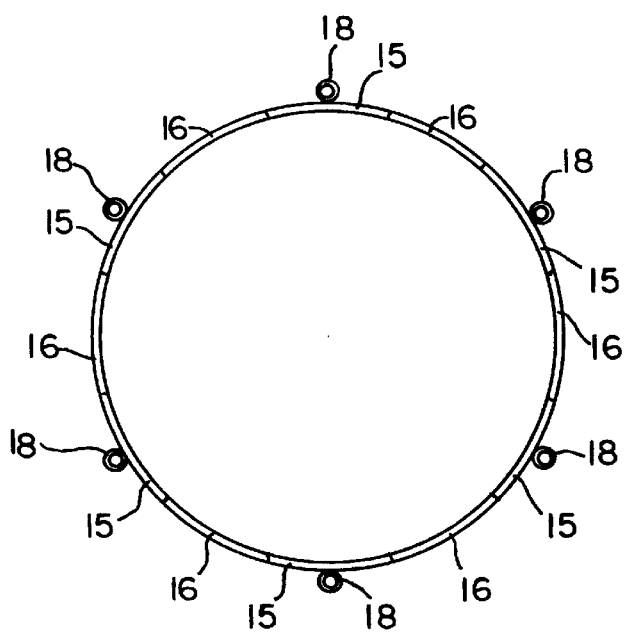
FIG. 2 is an enlarged, schematic end elevational view of the stent in its unexpanded configuration.
Figure 3:
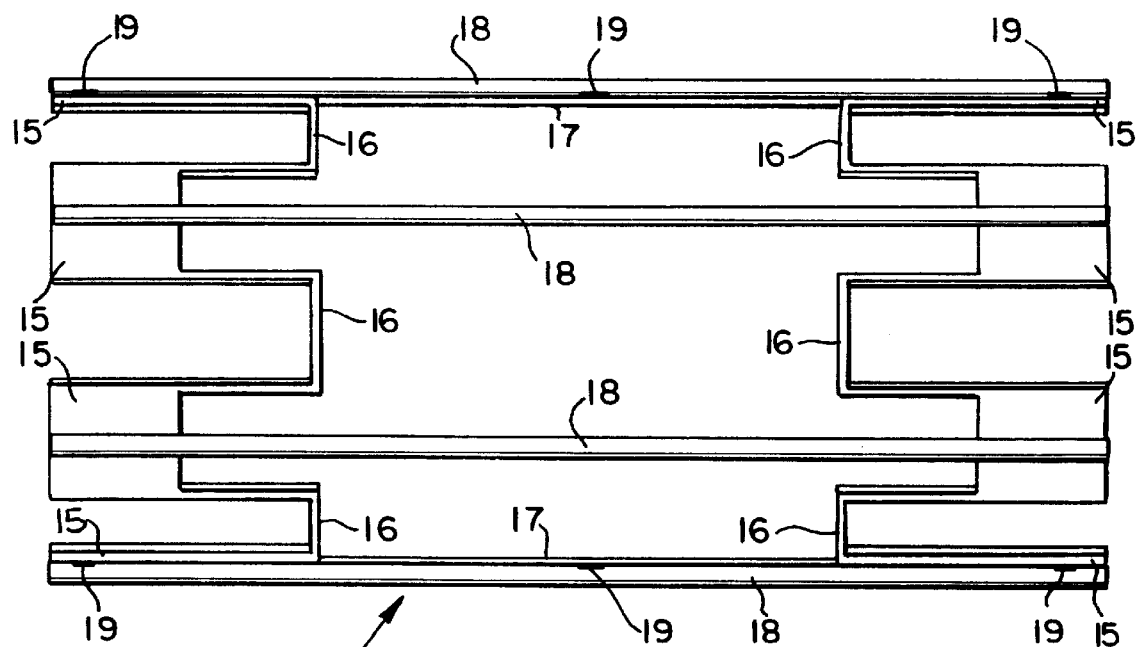
FIG. 3 is an enlarged, schematic side elevational view of the stent in its unexpanded configuration.

Referring to FIGS. 2 and 3, the stent 10 is in the form of a generally tubular mesh-like configuration providing a central lumen along its longitudinal axis. The generally tubular stent 10 includes a series of tab-like rigid supports 15 which are disposed in a generally similar arrangement at each end of the tubular stent 10. The rigid support tabs 15 of the stent are generally equally spaced apart around the circular perimeter at each end of the stent 10. In addition, the rigid support tabs 15 are disposed so that a rigid support tab 15 at one end of the stent is substantially opposite a corresponding rigid support tab 15 at the other end of the stent 10. Spacer bars 17 connect each rigid support tab 15 at one end of stent 10 to an opposite corresponding rigid support tab 15 at the other end of the stent. The spacer bars 17 serve as struts to prevent the stent from foreshortening along its longitudinal axis. Each spacer bar 17 thereby serves to maintain corresponding pairs of support tabs 15 at opposite ends of the stent in position relative to the longitudinal axis of the tubular stent. The spacer bars are also sufficiently rigid to resist bowing or bending in the transverse direction relative to the stent. As shown schematically in FIG. 2, the support tabs 15 at each end of the stent are positioned adjacent to one another in a generally annular arrangement around the periphery of each end of the stent so that each support tab 15 has a diametrically opposing support tab 15 at each end of the stent. A series of deformable connecting links 16 in the form of plastically-deformable, U-shaped, wire-like links are used to connect adjacent rigid support tabs 15 around the annular arrangement of the support tabs at each end of stent 10, so that the stent 10 can be diametrically expanded through plastic deformation of the connecting links 16. As the stent is diametrically expanded, the connecting links 16 bend so that the stent maintains its generally tubular shape. The central lumen of the stent widens but the spacer bars 17 inhibit longitudinal movement of the support tabs thereby maintaining the overall length of the stent. The stent 10 may be expanded by applying a radially, outwardly extending force from the exterior of the stent. For this purpose, external expansion couplings, in the form of coupling tubes 18, are oriented longitudinally relative to the stent and are attached on the spacer bars 17 along the outside of the stent 10. For example, the coupling tubes 18 can be fabricated from 0.5" (12.7 mm) lengths of 26 gauge hypodermic tubing and attached with laser welds 19 to the exterior of the spacer bars 17 and the support tabs 15, making sure that the lumen of each coupling tube 18 remains open and intact. Alternatively, the stent 10 may be fabricated by extruding the stent 10 as one piece. Deployment of stent 10 may then be effected using the delivery apparatus 8. The coupling tubes 18 permit the stent 10 to be removably mounted on the stent deployment mechanism 40 of the stent delivery apparatus 8. The coupling tubes 18 also serve the purpose of reinforcing the spacer bars 17 to inhibit compression and/or expansion of the stent along its longitudinal axis thereby functioning as a strut and to inhibit bending or collapsing of the stent in the transverse direction. In an alternative arrangement, the coupling tubes 18 may be used instead of the spacer bars 17 with the ends of the coupling tubes being attached, by laser welding, to the corresponding support tabs 15 at opposite ends of the stent thereby serving the function of the spacer bars 17. In yet another alternative arrangement, the stent may be used without the coupling tubes 18 in which case the stent can be expanded from the inside at the target location using a balloon-type catheter delivery system. Since the stent is plastically deformed, there is very little recoil and the stent resists being recompressed.

In a particular embodiment, the stent 10 is fabricated from a single piece of continuous tube with no welds or solder points. For example, a 316L grade seamless stainless steel tube with an outer diameter of 0.125" (3.175 mm), a nominal wall thickness of 0.006" (0.1524 mm), and an overall length of 0.5" (12.7 mm) may be used. Six rectangular regions of material are removed from each end of the tube so that material remains for six rigid support tabs 15. The support tabs are thin, generally arcuate, and conform in shape to the stent in the first direction. Deformable connecting links 16 and spacer bars 17 are formed by removing six generally H-shaped regions 11 from the central portion of the tube thereby forming open areas in the tubular stent. Thus, the stent 10 has a general tubular structure having a thin-walled lattice frame with openings in the frame. Wire electrical discharge machining or wire EDM can be used for removing sections of the tubing to extremely high precision without creating burrs or deformations. The wire diameter for cutting can be approximately 0.010" (0.254 mm) resulting in corners that are radiused to 0.005" (0.127 mm). Using this method a stent 10 can be made with rigid support tabs 15 that are 0.0625" (1.588 mm) long by 0.0625" (1.588 mm) wide, spacer bars 17 that are 0.374" (9.5 mm) long by 0.020" (0.508 mm) wide and connecting links 16 that are 0.004" (0.102 mm) wide relative to the circumference of the stent. After full expansion, the stent 10 can assume a final diameter of approximately 0.315" (8.0 mm) or 2.5 times its original diameter.

The total intimal surface area along a stented segment of a vessel can be approximated from the equation for the surface area of a tube, or $\pi d l$, where d is the stent diameter and l is the stent length. For a stented region corresponding to the stent 10 of the type shown schematically in FIG. 3 with the above dimensions, the estimated total intimal surface area is $\pi(8.0)(12.7)=319.20$ mm$^2$. The total surface area of the stent, with coupling tubes made from 26 gauge hypodermic tubing, that can be exposed to the vessel lumen is estimated to be 99.02 mm$^2$. Using geometrical constraints, the area of metallic surface in contact with intimal tissue is estimated to be 54.43 mm$^2$. Expressed in terms of percent open area within the stented segment, the stent of the present invention is therefore estimated to be 82.95% open. This result suggests that the stent of the present invention is capable of preserving a large area of endothelialized tissue. In addition, the amount of metallic surface exposed to the blood is kept relatively low.

Construction of the stent 10 is not limited to stainless steel. The stent 10 can be made from any material which is compatible with the human body and any bodily fluids that the stent 10 may contact. However, the stent 10 must be made from a material that allows for expansion of stent 10 and must be able to maintain its expanded shape while disposed within the lumen of the body passage. In addition to stainless steel, suitable materials for construction of stent 10 may include tantalum and titanium. The stent 10 can also be fabricated from a memory metal such as nitinol. In addition, the stent 10 does not have to be fabricated from a single piece of continuous tube. For example, the spacer bars 17 and/or the connecting links 16 can be made separately from the rigid support tabs 15 and attached using, for example, laser welding techniques. Alternatively, the stent 10 may be fabricated by extruding the stent 10 as one piece.

Figure 4A:
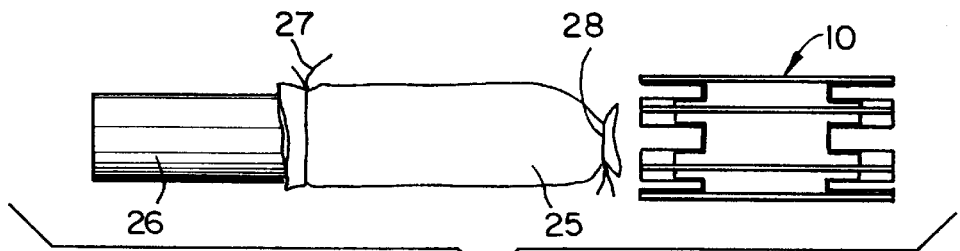
FIG. 4a is an enlarged side elevational view of the stent and a tool having a vein segment thereon, depicting a method for attaching the vein segment to the stent, using tissue adhesive, just prior to insertion of the vein segment within the lumen of the stent.
Figure 4B:
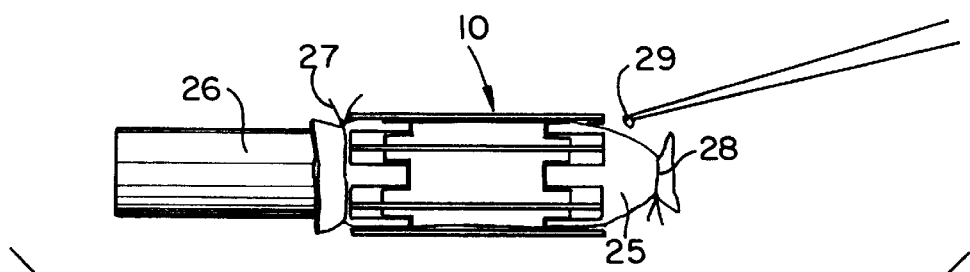
FIG. 4b is an enlarged side elevational view of the stent and a tool having a vein segment thereon, depicting a method for inserting the vein segment into the lumen of the stent and for attaching the vein segment to the stent using tissue adhesive, just prior to inflation of the vein segment within the stent.
Figure 4C:
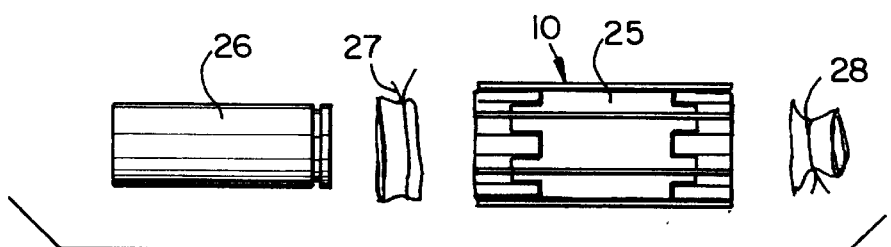
FIG. 4c is an enlarged side elevational view of the stent with the vein segment inserted within the lumen of the stent, depicting a method for attaching a vein segment to the stent using tissue adhesive, following curing of the tissue adhesive.

While the stent may be deployed as a "stand alone" device, the stent may also be effectively used as a vascular endograft by attaching a segment of vein, preferably an autologous vein or a synthetic graft material within the central lumen of the stent. Preferably, an autologous vein segment is utilized to provide an endothelial layer as a lining for the lumen of the stent. As shown in FIGS. 4a–4c, a vein segment 25 may be attached to the inner surface of the stent 10 by, for example, using tissue adhesive 29. As shown in FIG. 4a, the vein segment 25 is attached to a piece of tubing 26 with suture 27, which is in turn attached to a syringe filled with isotonic saline. The free end of the vein segment 25 is then closed with suture 28. The vein segment 25 is deflated using the syringe and, as shown in FIG. 4b, the vein segment is then inserted into the lumen of the stent 10. A small amount of tissue adhesive 29 is applied to multiple points along the inner surface of the stent 10. As shown in FIG. 4c, the vein segment 25 is then inflated so that the outer surface of the vein segment 25 contacts the inner surface of stent 10 especially at the points where tissue adhesive 29 has been applied. Once the tissue adhesive 29 has cured, the vein segment 25 is disconnected from the tubing 26 and the excess vein segment 25 is trimmed at each end of the stent.

Figure 5:
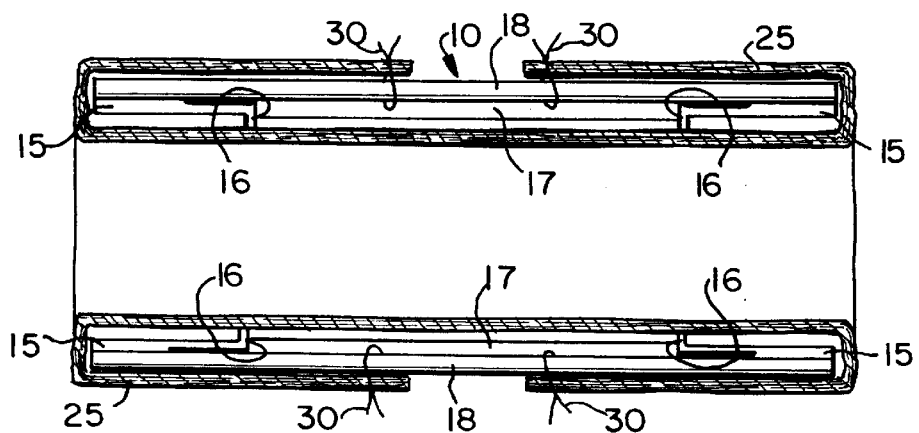
FIG. 5 is an enlarged cross sectional view of the stent showing a vein segment attached to the stent with sutures.

The use of tissue adhesive to secure the vein segment to the stent may not always be suitable or permitted. Accordingly, a vein segment may be attached to the stent 10 in accordance with a preferred method of using sutures 30. As shown in FIG. 5, a length of vein segment 25 about twice as long as the length of stent 10 is used. The vein segment 25 is inserted within the lumen of stent 10 so that the stent is generally centered about the vein segment 25. The ends of the vein segment 25 are then everted over the ends of stent 10 so as to completely line the inner surface of stent 10 and to substantially cover the outer surface of stent 10. After slightly crimping the stent 10 onto the external surface of the vein segment 25, the proximal and distal ends of the vein segment 25 are secured to the adventitia with interrupted 7.0 proline sutures between each spacer bar 17. Accordingly, a stent-vein complex is provided for deployment at the target location by the stent delivery apparatus 10.

The stent delivery apparatus 8 includes a stent deployment mechanism 40, as shown in FIGS. 6 and 7, manually operated by drive unit 48, as shown in FIG. 8. The drive unit 48 (Edmund Scientific, Barrington, N.J., model #J3650) is connected with the stent deployment mechanism 40 by control cable 49. The stent deployment mechanism 40 includes a series of six spokes 42 each connected at one end to a bushing 43. The spokes 42 may be in the form of a symmetric bundle of six spring steel wires of diameter 0.008 inches (0.203 mm) bonded to the outer wall of the bushing 43 which is in the form of a 316L grade stainless steel tube having a length of approximately 0.25 inches (6.35 mm), an outer diameter of 0.0732 inches (1.86 mm) and an inner diameter of 0.05 inches (1.28 mm). The free ends of the spokes removably nest within conical tip 45 disposed at the end of a central guidewire 44 in the form of stainless steel wire having a diameter of 0.04 inches (1 mm). When the guidewire 44 is moved to retract the tip 45 toward the cable 49, the free ends of the spokes can be positioned to nest within the tip 45. When the guidewire 44 is moved to displace the tip 45 away from the cable 49 the free ends of the spokes 42 are released as shown in FIG. 6.

In cable 49, the central guidewire 44 is coaxially contained within a flexible guide tube 41 in the form of a polymer tubing, such as flexible nylon tubing having the same inner and outer diameters as the bushing 43. The bushing 43 is bonded to one end of the guide tube 41 using, for example, epoxy, spot welding, or soldering techniques. The junction between the bushing 43 and the guide tube 41 is enclosed within an external junction sleeve 39 in the form of a stainless steel tube segment. The other end of the flexible guide tube extends with the guidewire 44 approximately 30 inches to the drive unit 48 shown in FIG. 8. The drive unit functions to displace the guidewire 44 through the flexible guide tube 41 in a controlled manner by manual rotation of actuator knob 38. The guidewire 44 and the flexible guide tube 41 are enclosed within an outer sheath tube 46 in the form of a polymer tube such as a clear polyethylene or teflon tubing that is approximately 30 inches long. As best shown in FIGS. 1 and 6, the end of the sheath tube 46 at the stent deployment mechanism is capped by a sheath cap 47 in the form of 316L grade stainless steel tubing having a length of approximately 2 inches. The sheath cap 47 serves as a rigid housing for accommodating the wire spoke bundle 42 when the sheath cap is slid over the wire spoke bundle. The sheath tube 46 may be manually retracted relative to flexible tube 41 and guidewire 44 to displace the sheath cap 47 from the wire spoke bundle 42 in order to expose the wire spoke bundle. Flexible tube 41, guidewire 44, and outer sheath 46 are concentric and allowed to move relative to each other along their axes.

The proximal ends of flexible tube 41 and guidewire 44 are attached to the linear microdrive unit 48, which allows for the axial movement of guidewire 44 relative to flexible tube 41. As knob 38 is turned an internal rack and pinion drive mechanism longitudinally displaces the central guidewire 44 relative to the flexible inner tube 41. As schematically depicted in FIG. 9a, when the tip 45 of the guidewire 44 is positioned in its mid-position the free ends of the spokes 42 are captured within the tip 45 but the spokes remain relatively extended, or unflexed, between the tip 45 and the bushing 43. As schematically depicted in FIG. 9b, when the guidewire 44 is deployed so the tip 45 moves toward the bushing 43 at the distal end of flexible tube 41, spokes 42 are caused to bend and flex outwardly.

Figure 11:
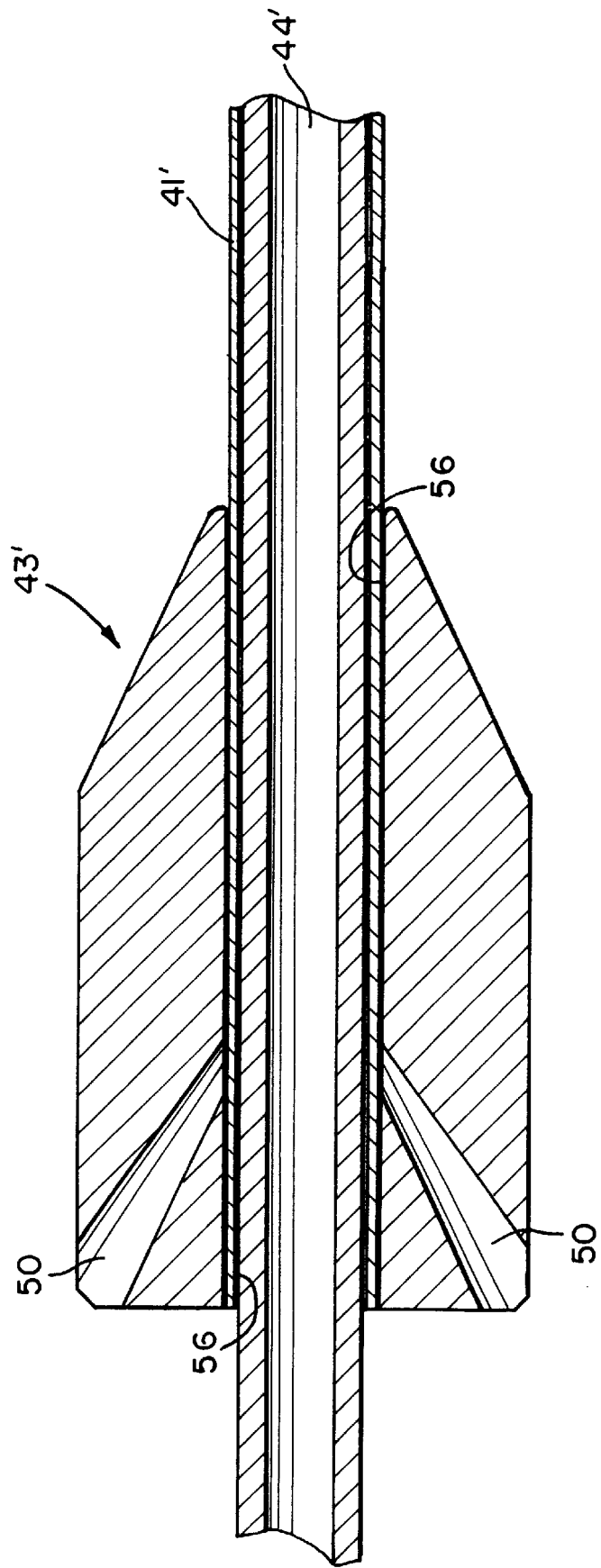
FIG. 11 is an enlarged, cross-sectional view of a bushing for the stent deployment mechanism for guiding movement of the wire spokes in accordance with another embodiment of the present invention.

In an alternative embodiment of the stent deployment mechanism, the spokes 42 are attached to flexible tube 41' by bushing 43', as depicted in FIG. 11, which serves as a bushing for the guidewire 44'. The spokes 42 may be made from spring steel wires of diameter 0.008" (0.203 mm). The bushing 43' is a brass cylindrical section with a frustaconical end having an outer diameter of 0.138" (3.5 mm), an inner diameter of 0.042" (1.079 mm), and a length of 0.335" (8.5 mm). An inner bore 56 is provided through the bushing to permit the flexible tube 41' and the guidewire 44' to pass therethrough. The cross section of the inner bore 56 of bushing 43' is not circular but instead includes flattened sidewall sections to prevent the bushing 43' from rotating around the flexible tube 41'. The flexible tube 41' is made from ABS plastic tubing with an approximate 3" (76.2 mm) length of the distal end of the flexible tube 41' being shaped with flattened sidewall sections to mate with inner bore 56. Six small angled bores 50 are drilled at 30° relative to the longitudinal axis of the bushing at the distal end of the bushing 43'. The bores 50 are approximately 0.010" (0.254 mm) in diameter and widen to approximately 0.020" (0.005 mm) at the periphery of the bushing. The bores are substantially equally spaced around the distal end of the bushing 43' to accommodate the spokes 42, which are epoxy glued in place within the bores 50. The bushing 43' is epoxy bonded about the distal end of the flexible tube 41'. The flexible tube 41' extends from the bushing for 30" before being connected to the linear microdrive unit 48. In addition, the outer sheath 46 is constructed from teflon tubing approximately 30" (76.2 cm) in length with an inner diameter sufficiently large to form a slip fit over the bushing 43'. Attached to the distal end of the outer sheath 46 is a tubular end cap 47 which is fabricated from a 316L grade stainless steel tubing approximately 2" (50.8 mm) in length and with similar inner and outer diameters to the outer sheath 46. The end cap 47 serves as a rigid housing that accommodates spokes 42 when the spokes 42 are withdrawn sufficiently into the end cap 47.

Figure 12:
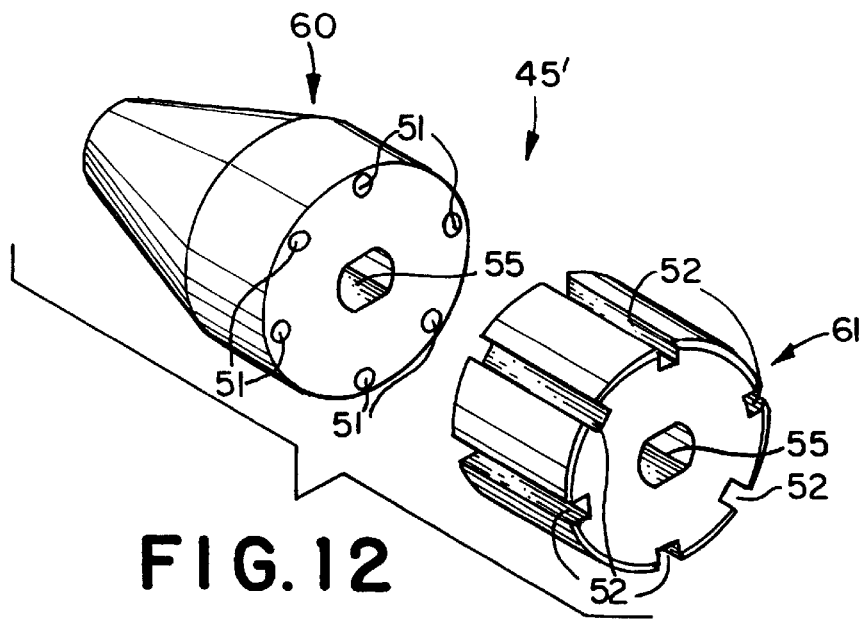
FIG. 12 is an enlarged, exploded perspective view of the frustaconical tip of the stent deployment mechanism for receiving the free ends of the wire spokes for use with the bushing shown in FIG. 11.
Figure 13:
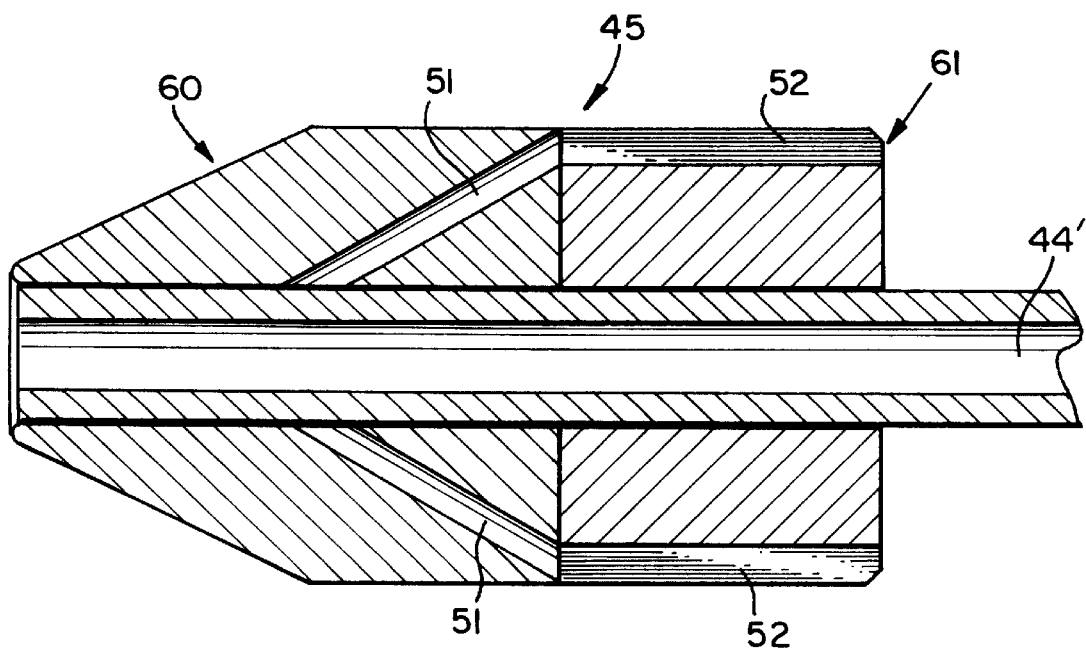
FIG. 13 is an enlarged, cross-sectional view of the frustaconical tip shown in FIG. 12.

As depicted in FIGS. 12 and 13, a frustaconical tip 45' of the catheter is used in conjunction with the bushing 43' depicted in FIG. 11. The tip 45' is fabricated from two brass sections, 60 and 61, having outer diameters of approximately 0.138" (3.5 mm) and inner diameters of approximately 0.042" (1.079 mm). The first section is generally cylindrical with a frustaconical end. The second section is generally cylindrical. A central aligned bore 55 extends through the second section and into the first section. The cross section of the inner bores 55 of the two tubular sections 60 and 61 are not circular but instead have flattened sidewall sections, as shown in FIG. 12, to prevent the tip 45' from rotating around the guidewire 44'. The guidewire 44' is made from narrow hypodermic tubing with an approximately 3" (76.2 mm) length of the distal end of the guidewire 44' being shaped with flattened exterior sidewall sections to mate with inner bore 55. The first section 60 of the tip 45' has a length of approximately 0.236" (6 mm) and the second section 61 of the tip 45' has a length of 0.010" (2.5 mm). Six small radially oriented bore holes 51, approximately 0.020" (0.508 mm) in diameter, are drilled at 30° angles relative to the longitudinal axis of the central bore 55. The bore holes 51 are uniformly spaced around the proximal end of the first section 60 to accommodate the free ends of the spokes 42, which are loosely held in place. Small exterior longitudinal slots 52, 0.020" (0.508 mm) deep and 0.020" (0.508 mm) wide, are milled along the second section 61 to act as guide slots for the spokes 42. The longitudinal slots 52 confine the movement of the spokes 42 to a radial direction in a plane through the longitudinal axis of the second section 61 and inhibit lateral movement of the spokes 42 out of the plane. The proximal end of the first section 60 is held by friction fit on the end of the guidewire 44' in abutment with the distal end of the second section 61, so that the slots 52 along the second section 61 register with the bore holes 51 drilled in the first section 60. Alternatively, the first section 60 and the second section 61 can be attached using epoxy or spot welding techniques.

Yet another embodiment of the stent deployment mechanism 40 is depicted in FIGS. 15–18. The bushing 143 is fabricated from two abutting brass sections, 173 and 174. The first section 173 has a larger cylindrical portion at the distal end that tapers into a frustaconical section which terminates in a smaller cylindrical section at the proximate end of the first section. The second section 174 is generally cylindrical. The two abutting sections 173 and 174 have outer diameters of 0.138" (3.5 mm), inner diameters of 0.042" (1.079 mm), and a combined overall length of 0.335" (8.5 mm). An inner bore 156 passes through both sections. The cross section of the inner bore 156 of the two tubular sections 173 and 174 is sized and shaped to mate with the distal end of the flexible tube 41 and to prevent the bushing 143 from rotating around the flexible tube 41. The second section 174 has a circular groove 182 milled into the proximal end of the second tubular section 174. The circular groove 182 is concentric with the inner bore 156. In addition, small external longitudinal slots 180 are milled along the second tubular section 174. A series of six swing arms 176, having spoke support tubes 177 attached to ball bearings 178, serve as hinges and are disposed with the ball bearings 178 positioned within the circular groove 182, which serves as a bearing race, and the spoke support tubes 177 aligned with the longitudinal slots 180. The swing arms 176 and longitudinal slots 180 confine the movement of the spokes 42 to a radial direction in a plane through the longitudinal axis of the second section 174 and inhibit lateral movement of the spokes 42 out of the plane. The distal end of the first tubular section 173 is then abutted against the proximal end of the second tubular section 174 thereby capturing the ball bearings 178 within the bearing race groove 182 to hold the swing arms 176 in place. The first tubular section 173 is attached to the second tubular section 174 by glue, epoxy, laser welding, or any other suitable means. Ends of the spokes 42 are then inserted into the spoke support tubes 177 and are held in place by epoxy, glue, laser welding, or any other suitable means.

Figure 16:
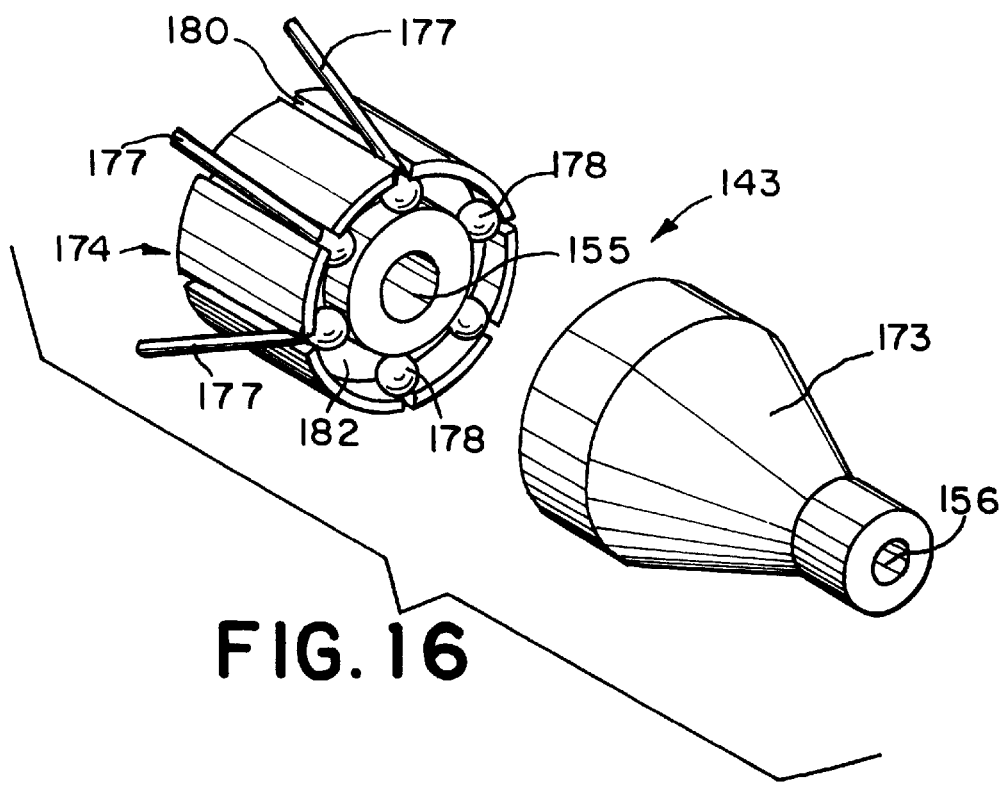
FIG. 16 is an enlarged, exploded perspective view of a bushing for the stent deployment mechanism shown in FIG. 15.
Figure 17:
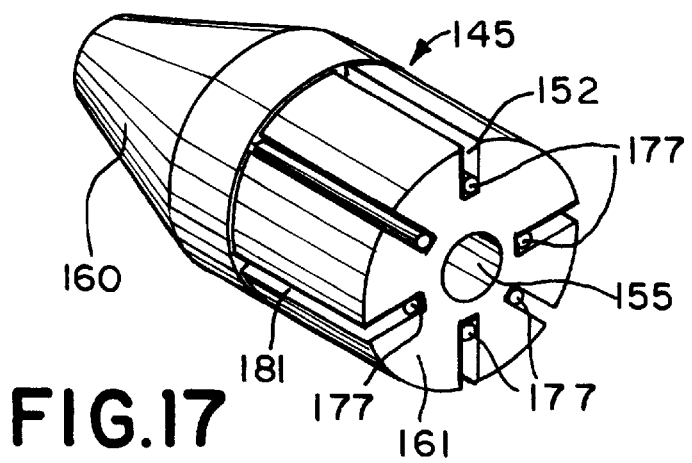
FIG. 17 is an enlarged, exploded perspective view of the frustaconical tip of the stent deployment mechanism shown in FIG. 15.
Figure 18:
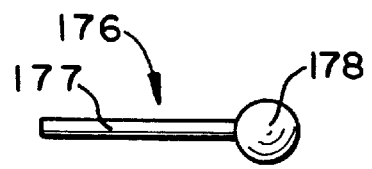
FIG. 18 is an enlarged side elevational view of a swing arm for the stent deployment mechanism shown in FIG. 15.

As depicted in FIG. 17, the frustaconical tip 145 of the catheter for use in conjunction with the bushing 143 shown in FIG. 16 is fabricated from a first section 160 of brass having a cylindrical section terminating in a frustaconical point and an abutting second generally cylindrical section 161 of brass. The two sections 160 and 161 have outer diameters of 0.138" (3.5 mm), and inner diameters of 0.042" (1.079 mm) and an overall combined length of 0.335" (8.5 mm). An inner bore 155 extends through the second section 161 and into the first section 160. The inner bore 155 of the tubular sections 160 and 161 is sized and shaped to accommodate the distal end of the guidewire 44 and to prevent the tip 145 from rotating around the guidewire 44. The second section 161 of the tip 145 is identical to the second section 174 of the bushing 143. As with the bushing 143, a series of swing arms 176, having spoke support tubes 177 attached to ball bearings 178, serve as hinges and are disposed with the ball bearings 178 positioned within the circular groove 182 serving as a bearing race and the spoke support tubes 177 aligned with the longitudinal slots 180. The swing arms 176 and the longitudinal slots 180 confine the movement of the spokes 42 to a radial direction in a plane through the longitudinal axis of the second section 174 and inhibit lateral movement of the spokes 42 out of the plane. The proximate end of the first section 160 is then abutted against the distal end of the second section 161 thereby holding the swing arms 176 in place. The first section 160 is secured to the second section 161 by glue, epoxy, laser welding, or any other suitable means. The free ends of spokes 42 can then be inserted into the spoke support tubes 177 where they are releasably held in place.

Figure 19A:
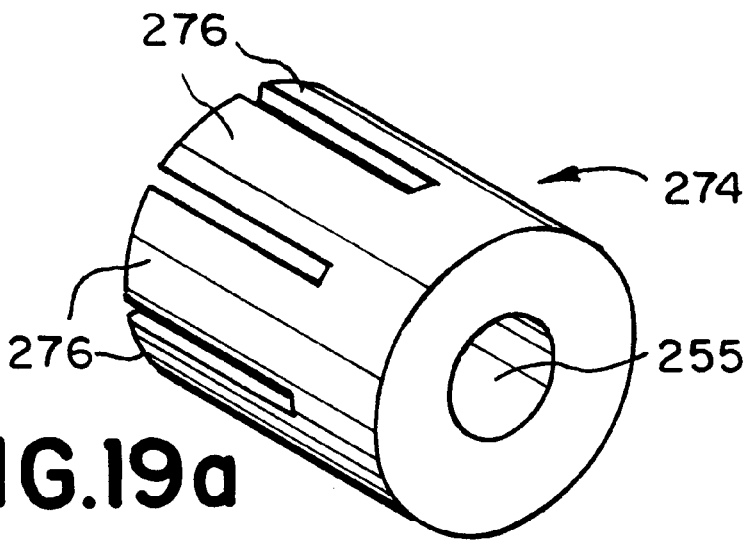
FIG. 19a is an enlarged, schematic perspective view of a bushing in an unflexed position for a stent deployment mechanism in accordance with yet another embodiment of the present invention.
Figure 19B:
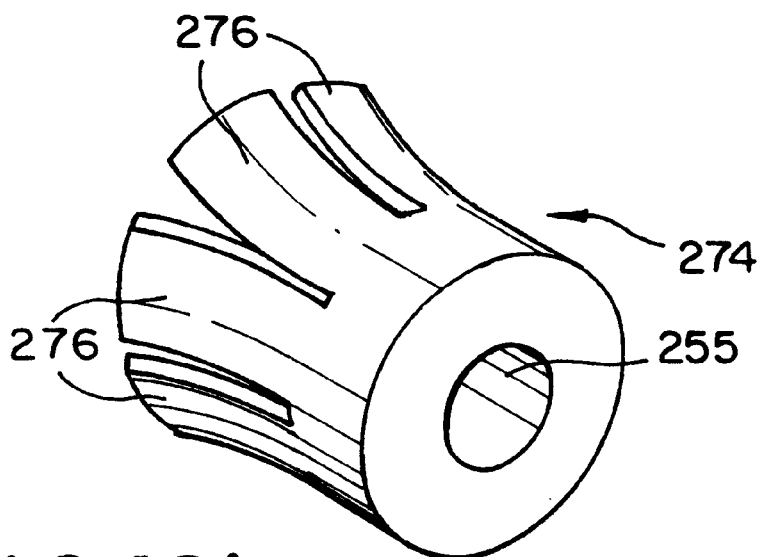
FIG. 19b is an enlarged, schematic perspective view of the bushing shown in FIG. 19a but in the flexed position.

In still another embodiment, the bushing and a proximate section of a frustaconical tip may be made from a tubular section 274 of flexible plastic or metal, as depicted in FIGS. 19a and 19b, to guide the movement of spokes 42. One end of the tubular section 274 is fluted with each flute 276 being sufficiently wide to prevent movement of the spokes 42 out of a plane through the longitudinal axis of the tubular section 274 and the longitudinal axis of the flute 276. The fixed ends of the spokes 42 are attached to the separated flutes 276 of the tubular section 274 used as the bushing by epoxy, glue, laser welding, or any other suitable means. The free ends of the spokes 42 may be releasably held in the flutes 276 of the tubular section 274 used in the frustaconical tip. When the bushing is moved longitudinally relative to the frustaconical tip by the drive unit 48 so as to shorten the distance between the bushing and the tip, the spokes 42 and the flutes 276 flex as shown in FIG. 19b. When the bushing is returned to its starting position relative to the tip, the spokes 42 and the flutes 276 return to their unflexed positions as shown in FIG. 19a.

Figure 14:
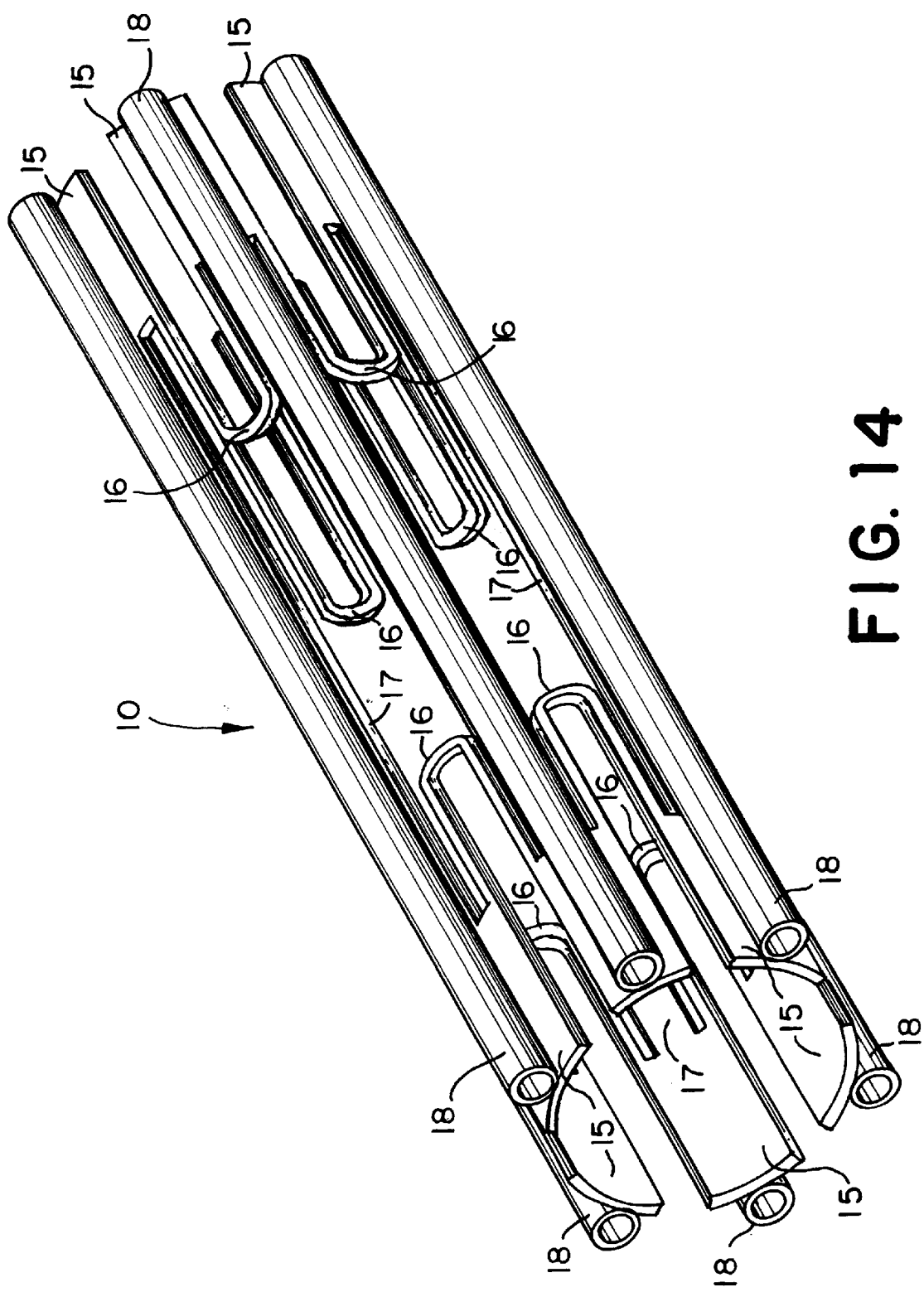
FIG. 14 is an enlarged perspective view of a stent in accordance with another preferred embodiment of the present invention.
Figure 15:
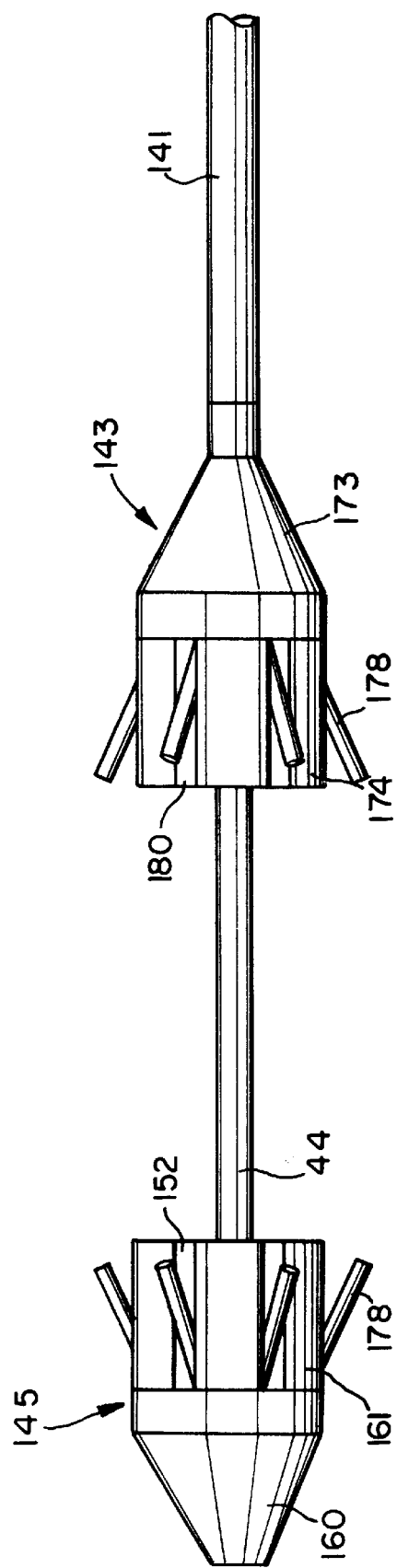
FIG. 15 is an enlarged side elevational view of a stent deployment mechanism having the wire spokes removed, located at the distal end of the delivery apparatus in accordance with another embodiment of the present invention.

As shown in FIG. 14, a stent 10 is depicted that is substantially similar to the stent shown in FIG. 1 except that the component parts of the stent 10 shown in FIG. 14 have different sizes relative to one another. For example, the coupling tubes 18 shown in FIG. 14 are somewhat oversized relative to the stent shown in FIG. 1. Also, the connecting links 16 shown in FIG. 14 are somewhat more rounded than the connecting links shown in FIG. 1. While the stent shown in FIG. 14 is presently a preferred configuration, both stents function in a similar manner.

Figure 10A:
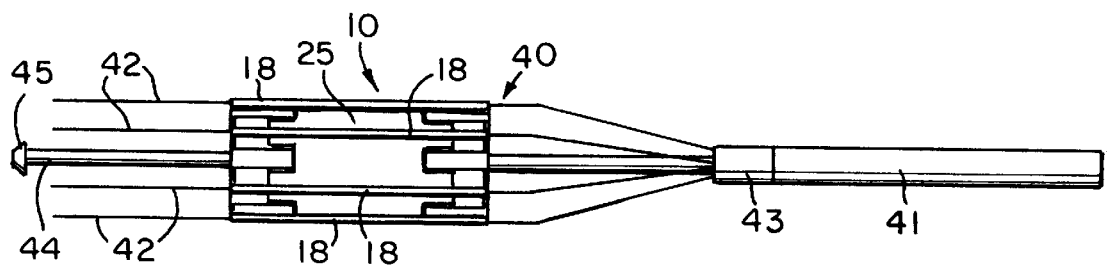
FIG. 10a is an enlarged side elevational view of the stent mounted on the stent deployment mechanism of the delivery apparatus in an unexpanded configuration.
Figure 10B:
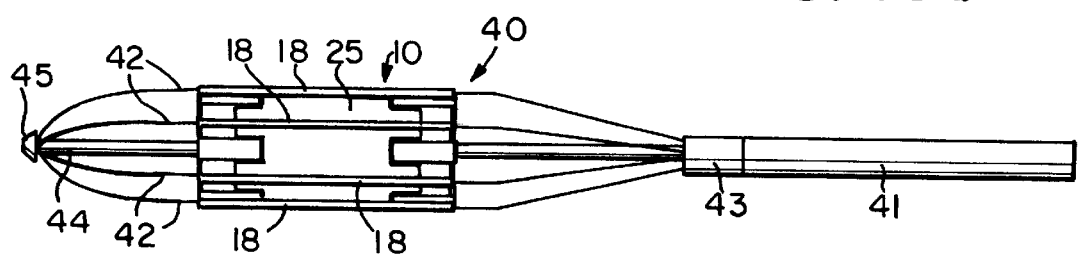
FIG. 10b is an enlarged side elevational view of the stent mounted on the stent deployment mechanism of the delivery apparatus with the wire spokes in position for expansion of the stent.
Figure 10C:
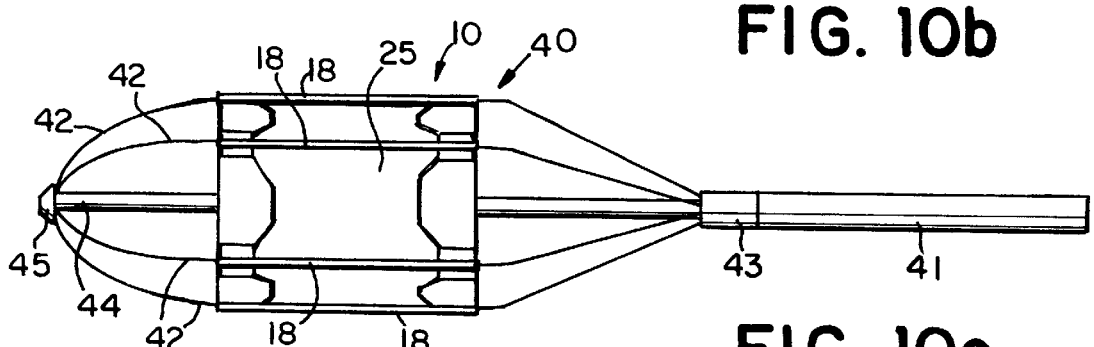
FIG. 10c is an enlarged side elevational view of the stent mounted on the stent deployment mechanism of the delivery apparatus following expansion of the stent.
Figure 10D:
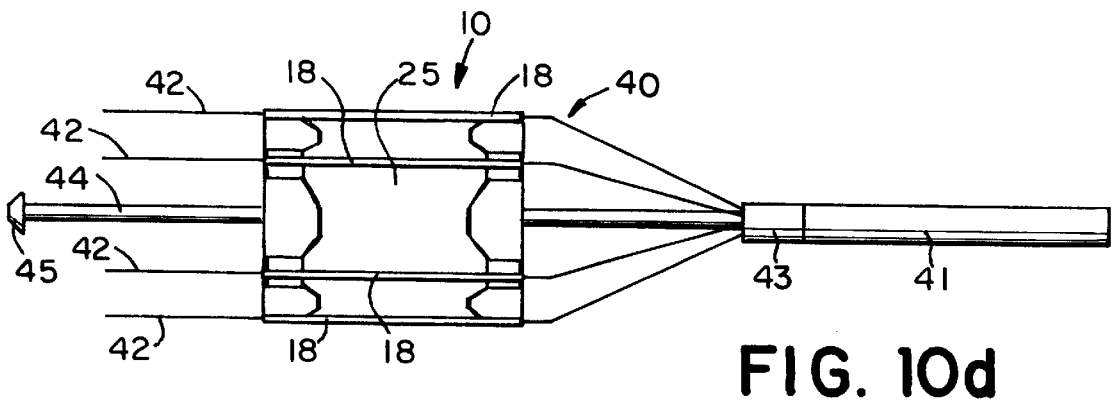
FIG. 10d is an enlarged side elevational view of the stent and the stent deployment mechanism of the delivery apparatus in position for removal of the stent deployment mechanism from the expanded stent while leaving the expanded stent within the lumen of the body passage.

In operation, a method of deploying the stent 10 is shown in FIGS. 10a–d. Referring to FIG. 10a, the stent 10 is first installed on the stent deployment mechanism 40. The spokes 42 are passed through the coupling tubes 18 with the guidewire 44 passing through the lumen of stent 10. If a vein segment is attached to the stent in the manner shown in FIG. 5, the spokes must poke through the portions of the vein segments that cover the openings to the coupling tubes 18. After the stent is properly positioned on the stent deployment mechanism 40, the free ends of the spokes 42 are manually nested within the tip 45 as shown in FIG. 10b. The outer sheath 46 is then slid over the stent 10 to cover stent 10. The tip 45 at the distal end of stent deployment mechanism 40 is then inserted into the body and moved to the target location within the body passage. The outer sheath 46 is then pulled back to expose the stent 10 and the stent deployment mechanism 40 at the target location. The drive unit 48 is then actuated to displace tip 45 in a direction toward the bushing 43 at the end of flexible tube 41 causing the spokes 42 to flex radially outward thereby exerting an external, radially outward force that expands the stent 10 as shown in FIG. 10c. Once the stent 10 is expanded to the desired diameter, plastic deformation of the connecting links causes the stent to remain in its expanded configuration providing a radially enlarged central lumen. After the stent has been expanded, the tip 45 is displaced by the drive unit in a direction away from the bushing 43 at the distal end of flexible tube 41 thereby releasing the free ends of the spokes 42 from the tip 45 as shown in FIG. 10d. The guidewire 44, the flexible tube 41, and the outer sheath 46 are then withdrawn while leaving the stent 10 in position within the body passage.

EXAMPLES

Example 1

A stent of the type shown in FIG. 2 was tested by implantation in the left external iliac artery of mongrel dogs. The stent was tested for structural integrity, deformability, migration, and patency.

Five adult male mongrel dogs were used for the study. The animals were placed under general inhalational anesthesia with a halothane/oxygen mixture, and administered an intravenous dose of a preoperative cephalosporin. Both groins were shaved and prepped with betadine and alcohol prior to being draped in the usual sterile fashion. Incisions measuring approximately 2–3 cm were made vertically overlying the femoral vessels. The femoral artery was isolated and controlled with vessel loops. At this time, intravenous heparin was administered at a dose of 100 u/kg. A transverse arteriotomy was made and a 12 ft. (3.66 m) sheath introduced within the artery. A stent according to the present invention was mounted on a 0.315" (8 mm) diameter balloon (1.57" (4 cm) in length) which was attached to the end of a catheter. The stent was positioned in the left external iliac artery (approximately 1.97" (5 cm) from the aortic bifurcation) under fluoroscopic guidance. The stent was then expanded by inflating the balloon uniformly to 10 atmospheres. Upon completion of the procedure, an arteriogram was performed. The femoral artery was ligated and the incision closed.

After a six week convalescent period, a final arteriogram was performed via a left brachial artery approach. The gradient of pressure across the stent was then assessed with measurements that were taken just distal to the stent, within the center of the stent and just proximal to the stent. All measurements were also compared with a baseline pressure value within the aorta near its bifurcation. The aorta was then cannulated for the purpose of pressure-perfusion fixation of the iliac vessel with a 2% paraformaldehyde mixture. The stent was subsequently harvested within the vessel and submitted for embedding in methyl methacrylate for future sectioning and histologic analysis.

The results indicate that the stent of the present invention is deployable using a balloon mounted to a catheter and that the stent was patent at the completion of the study. Also, there was no indication of migration or deformation of the stent by arteriographic analysis. Further, there was no gross evidence of exaggerated neointimal hyperplasia in any area of the stent lumen or any pressure gradient (defined as a change greater than or equal to 15% of the systolic blood pressure).

Example 2

A vein-lined stent, of the type as shown in FIG. 5, was subjected to conditions of high flow and high pressure in a bench top flow system to evaluate the effectiveness of a vein-lined stent.

A superficial femoral vein was harvested from a dog using standard sterile techniques. A segment measuring approximately 0.79 in. (2 cm) in length was selected without branches and immersed in normal saline. The vein was mounted on a moistened 14Fr dilator with care being taken not to injure the endothelial surface. The stent was then slid over the vein segment. After slightly crimping the stent onto the external surface of the vein, the ends of the vein were everted and secured to the adventitia with interrupted 7.0 proline sutures between each stent spacer. The stent-vein assembly was mounted onto an 0.315" (8 mm) balloon catheter and deployed within a transparent and compliant elastomeric tube that simulated a vessel. The entire apparatus was then subjected to a continuous flow of isotonic saline at pressures between 15 and 200 mmHg.

Qualitative observation of the stent-vein assembly in the continuous flow field showed that even under high pressure, there was no flow around the outside of the stent. The excellent seal made by the stent-vein assembly against the vessel wall was due primarily to the eversion of the ends of the vein over the stent. The seal was evidenced by micro bubbles which remained stationary on the outer surface of the stent in the flow field. The vein remained taut and stationary over the stent and there was no indication of stent or tissue migration.

Example 3

The bulk elastic behavior of the stent of the type shown in FIG. 2 was evaluated by mounting the stent within a compliant tube and subjecting the stent to increasing external pressures. The luminal area of the stent was recorded at each pressure. Pressure was then plotted against area reduction to estimate the stiffness, or inversely, the compliance of the stent.

The apparatus for loading the stent essentially comprised a compliant vessel with an inner diameter of 0.315" (8 mm), a pressure chamber for housing the vessel and the stent, a pressure transducer, and a video camera. The compliant tubes were custom manufactured using Dow Corning Sylgard 184. A very thin layer (approximately 0.016" (0.4 mm)) of the material was applied in liquid state to a polished 0.315" (8 mm) diameter cylinder mandrel which was constantly rotating in an oven at 150° C. The application of the liquid Sylgard to the mandrel was carefully controlled to insure that the thickness of the tubes did not vary around the circumference or the length of the tubes. The tubes were removed from the mandrel after curing and then mounted in the pressure chamber. The stent was then mounted on a balloon catheter (0.315" (8 mm) O.D.) and expanded within the lumen of the tube. The compliant tube section containing the stent was supported from both ends by rigid plexiglass fittings. The tube lumen was open to atmospheric pressure while the pressure chamber represented the external environment of the compliant tube. This configuration ensured that only the stented segment deformed under pressure. Two additional ports in the pressure chamber served as access for the pressure transducer and the syringe for imparting pressure to the system.

After the pressure chamber was filled with water, a syringe was connected to the system. The pressure within the system was controlled by the syringe piston displacement and monitored by the pressure transducer. A video camera was focused on the segment of tube containing the stent. Pressure within the chamber was increased from atmospheric pressure in 500 pascal increments. At each incremental increase in the chamber pressure, a personal computer digitized the video frame of interest. This image was ported to an image processing program where the luminal area was measured. The test was stopped when the luminal area measurement had decreased by 10 mm$^2$. In order to determine stent compliance, the change in the stent cross-sectional area was plotted against the incremental pressure increases. Compliance C was estimated from the relation:

$$C=(A_2-A_1)/(P_2-P_1)$$

where $(A_2-A_1)$ is the incremental area change and $(P_2-P_1)$ is the incremental pressure change. Stiffness is defined as the inverse of compliance. It should be noted from this relation that compliance is independent of the stent length. The stent of the present invention showed an initially linear elastic behavior up to approximately 10.0 KPa. Between 10.0 KPa and 20.0 KPa, the stent began to deform more for the same incremental increase in pressure. This pressure-deformation behavior indicated that the yield point of the material had been reached and that the stent was deforming plastically rather than elastically. A linear regression was applied to the data points up to 10.0 KPa in order to determine the compliance of the stent in the elastic region of deformation. The slope of the regression fit represents the bulk stiffness and the inverse of this slope represents the compliance. This analysis yielded a stiffness of 5221.65 and a compliance of 0.0002. The significance of such a low compliance is that increased rigidity is considered desirable in a stent.

In summary, the above Examples indicate that a stent according to the present invention can be expanded within the lumen of a body passage and can be used to support an endothelial layer. As such, the stent should improve vascular patency rates in current applications for stents, such as obliterative disease, arteriovenous fistulas, intimal injuries, and aneurysmal disease. The stent should also reduce thrombogenesis and neointimal hyperplasia. The stent should also counteract recoil of the vessel wall following angioplasty. In addition, the stent may be deployed by the stent delivery apparatus that couples to the stent and exerts an outward force on the external surface of the stent thereby leaving the luminal environment of the stent undisturbed.

The delivery apparatus 8 is designed specifically for the deployment of the stent 10. However, the wire cage or basket of the delivery apparatus could be easily adapted for transcatheter extraction of urinary tract and biliary tract stones or for retrieval of intravascular foreign bodies. The wire cage of the delivery apparatus actively expands and tends to passively collapse. Additionally, the delivery apparatus of the present invention might also be modified to incorporate a high speed rotary device within the wire cage. The delivery apparatus could then be used for declotting prosthetic dialysis access grafts, central veins, or even pulmonary arteries.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An expandable, generally tubular, intraluminal stent comprising:
   a) a plurality of end supports disposed in a first ring at a first end of the tubular stent and in a second ring at a second end of the stent;
   b) a plurality of struts for connecting the end supports in the first ring with the end supports in the second ring to inhibit relative longitudinal displacement between end supports at opposite ends of the stent; and
   c) a plurality of connecting links linking adjacent end supports in the first ring and adjacent end supports in the second ring so that the stent may be radially expanded from a first smaller diameter to a second larger diameter.

2. The stent in accordance with claim 1 wherein said struts include spacer bars having a first end connected with an end support at the first end of the stent and a second end connected with an end support at the second end of the stent.

3. The stent in accordance with claim 1 wherein the end supports in the first ring are disposed so that each end support in the first ring is positioned diametrically opposed to another one of the end supports in the first ring and the end supports in the second ring are disposed so that each end support in the second ring is positioned diametrically opposed to another one of the end supports in the second ring.

4. The stent in accordance with claim 1 wherein all of the end supports in the first ring are linked together by said connecting links and all of the end supports in the second ring are linked together by said connecting links.

5. The stent in accordance with claim 1 wherein all of the end supports in the first ring are connected with corresponding end supports in the second ring by the struts.

6. The stent in accordance with claim 5 wherein all of the end supports in the first ring are linked together by said connecting links and all of the end supports in the second ring are linked together by said connecting links.

7. The stent in accordance with claim 1 wherein the stent includes a central lumen and wherein the stent holds a vein segment to line the central lumen.

8. The stent in accordance with claim 7 wherein the vein segment includes a synthetic graft material.

9. The stent in accordance with claim 7 wherein the vein segment includes an autologous vein.

10. The stent in accordance with claim 7 wherein the vein segment is longer than the stent and ends of the vein segment are everted over the exterior surface of the stent.

11. The stent in accordance with claim 1 wherein the end supports include thin, generally arcuate support tabs.

12. The stent in accordance with claim 11 wherein the arcuate support tabs have a radius of curvature that equals a radius of curvature of the stent when in the first diameter.

13. The stent in accordance with claim 11 wherein each ring includes six support tabs.

14. The stent in accordance with claim 1 wherein the connecting links link adjacent end supports in each respective ring and the struts connect end supports at the first end of the stent to corresponding end supports at the second end of the stent so that open areas are formed in the tubular stent between a pair of adjacent end supports and a respective connecting link at the first end of the stent and a pair of adjacent end supports and a respective connecting link at the second end of the stent and between a pair of adjacent struts connecting the pair of end supports at the first end of the stent to the corresponding pair of end supports at the second end of the stent.

15. The stent in accordance with claim 14 wherein each of the open areas extends generally from the first end of the stent to the second end of the stent when in the second enlarged diameter.

16. The stent in accordance with claim 1 wherein the connecting links link adjacent end supports in each respective ring and the struts connect end supports at the first end of the stent to corresponding end supports at the second end of the stent so that open areas are formed in the tubular stent between the ring of end supports and connecting links at the first end of the stent and the end supports and connecting links at the second end of the stent and between adjacent struts connecting the ring of end supports at the first end of the stent with the ring of end supports at the second end of the stent.

17. The stent in accordance with claim 16 wherein each of the open areas extends generally from the first end of the stent to the second end of the stent when in the second enlarged diameter.

18. The stent in accordance with claim 16 wherein the open areas extend at least over half the longitudinal length of the stent.

19. The stent in accordance with claim 1 wherein the tubular stent has an effective stent surface area covering the end supports, the struts, the connecting links and open areas between the end supports, the struts and the connecting links when the stent is in the second larger diameter and wherein the end supports, the struts, and the connecting links have a combined surface area that is not more than 30% of the effective stent surface area.

20. The stent in accordance with claim 19 wherein the stent includes a central lumen and wherein the stent holds a vein segment to line the central lumen.

21. The stent in accordance with claim 20 wherein the vein segment includes a synthetic graft material.

22. The stent in accordance with claim 20 wherein the vein segment includes an autologous vein.

23. The stent in accordance with claim 19 wherein the combined surface area is not more than 20% of the effective stent surface area.

24. The stent in accordance with claim 23 wherein the stent includes a central lumen and wherein the stent holds a vein segment to line the central lumen.

25. The stent in accordance with claim 24 wherein the vein segment includes a synthetic graft material.

26. The stent in accordance with claim 24 wherein the vein segment includes an autologous vein.

27. An expandable, generally tubular, intraluminal stent comprising:
   a) a plurality of end supports disposed in a ring at each end of the tubular stent, the end supports in each ring being generally uniformly spaced apart around each respective ring;
   b) a plurality of struts for connecting the ring of end supports at one end of the stent with the ring of end supports at the other end of the stent, each strut extending generally from a respective one of the end supports at one end of the stent to a corresponding end support at the other end of the stent to inhibit relative longitudinal displacement between corresponding end supports at opposite ends of the stent; and
   c) a plurality of connecting links linking adjacent end supports in each respective ring so that the stent may be radially expanded from a first smaller diameter enabling delivery of the stent into a selected body passageway having a lumen into a second enlarged diameter for positioning the stent in the lumen of the body passageway.

28. The stent in accordance with claim 27 wherein the stent includes a central lumen and wherein the stent holds a vein segment to line the central lumen.

29. The stent in accordance with claim 28 wherein the vein segment includes a synthetic graft material.

30. The stent in accordance with claim 28 wherein the vein segment includes an autologous vein.

31. The stent in accordance with claim 28 wherein the vein segment is longer than the stent and ends of the vein segment are everted over ends of the stent.

32. The stent in accordance with claim 27 wherein said struts include spacer bars having a first end connected with an end support at one end of the stent and a second end connected with an end support at the other end of the stent.

33. The stent in accordance with claim 27 wherein the end supports are disposed in the respective ring so that each end support is positioned diametrically opposed to another one of the end supports in the ring.

34. The stent in accordance with claim 27 wherein all of the end supports in a respective ring are linked together by said connecting links.

35. The stent in accordance with claim 27 wherein all of the end supports in one of the rings are connected with corresponding end supports in the other ring by the struts.

36. The stent in accordance with claim 27 wherein the end supports include thin, generally arcuate support tabs.

37. The stent in accordance with claim 27 wherein the connecting links link adjacent end supports in each respective ring and the struts connect end supports at one end of the stent to corresponding end supports at the other end of the stent so that open areas are formed in the tubular stent between the ring of end supports and connecting links at one end of the stent and the end supports and connecting links at the other end of the stent and between adjacent struts connecting the end supports at the one end of the stent with the end supports at the other end of the stent.

38. The stent in accordance with claim 37 wherein each of the open areas extends generally from one end of the stent to the other end of the stent when in the second enlarged diameter.

39. The stent in accordance with claim 37 wherein the open areas extend at least over half the longitudinal length of the stent.

40. The stent in accordance with claim 37 wherein the tubular stent has an effective stent surface area covering the end supports, the struts, the connecting links and the open areas when the stent is in the second larger diameter and wherein the end supports, the struts, and the connecting links have a combined surface area that is not more than 30% of the effective stent surface area.

41. The stent in accordance with claim 40 wherein the stent includes a central lumen and wherein the stent holds a vein segment to line the central lumen.

42. The stent in accordance with claim 41 wherein the vein segment includes a synthetic graft material.

43. The stent in accordance with claim 41 wherein the vein segment includes an autologous vein.

44. The stent in accordance with claim 40 wherein the combined surface area is not more than 20% of the effective stent surface area.

45. The stent in accordance with claim 44 wherein the stent includes a central lumen and wherein the stent holds a vein segment to line the central lumen.

46. The stent in accordance with claim 45 wherein the vein segment includes a synthetic graft material.

47. The stent in accordance with claim 45 wherein the vein segment includes an autologous vein.

* * * * *